(12) United States Patent
Okuda et al.

(10) Patent No.: US 7,820,636 B2
(45) Date of Patent: Oct. 26, 2010

(54) SUGAR INTAKE PROMOTERS

(75) Inventors: Hiromichi Okuda, Matsuyama (JP); Chie Morimoto, Matsuyama (JP); Kenji Kameda, Ehime (JP); Fumiki Harano, Kyoto (JP)

(73) Assignee: Otsuka Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 10/474,721

(22) PCT Filed: Mar. 20, 2002

(86) PCT No.: PCT/JP02/02638

§ 371 (c)(1),
(2), (4) Date: Oct. 14, 2003

(87) PCT Pub. No.: WO02/083087

PCT Pub. Date: Oct. 24, 2002

(65) Prior Publication Data

US 2004/0116373 A1   Jun. 17, 2004

(30) Foreign Application Priority Data

Apr. 13, 2001   (JP) ............................. 2001-115870

(51) Int. Cl.
*A61K 31/7076* (2006.01)
*A61K 31/522* (2006.01)
*A61K 31/52* (2006.01)

(52) U.S. Cl. .................... 514/45; 514/47; 514/263.37; 514/263.4

(58) Field of Classification Search ............ 514/45, 514/47, 263.37, 263.4
See application file for complete search history.

(56) References Cited

U.S. PATENT DOCUMENTS 5,254,331 A * 10/1993 Mausner .................... 424/59

FOREIGN PATENT DOCUMENTS

| EP | 0 256 472 A2 | 2/1988 |
|---|---|---|
| EP | 256 472 | * 2/1988 |
| EP | 0 685 229 A1 | 12/1995 |
| EP | 0 722 734 A1 | 7/1996 |
| EP | 0 930 069 A2 | 7/1999 |
| JP | 47-26687 | * 7/1972 |
| JP | 47-026687 B | 7/1972 |
| JP | 4726687 A | * 7/1972 |
| JP | 47026687 | * 7/1972 |
| JP | 59-134706 A | 8/1984 |
| JP | 01-275511 A | 11/1989 |
| JP | 07-233037 A | 9/1995 |
| JP | 08-291018 A | 11/1996 |
| JP | 09-295915 A | 11/1997 |
| JP | 10-182412 A | 7/1998 |
| JP | 2001-31549 | 2/2001 |
| WO | WO 92/20341 | 11/1992 |

OTHER PUBLICATIONS

Japanese Society of Nutrition and Food Science, 53$^{rd}$ Conference, English Translation, 1999., p. 1.*
Japanese Society of Nutrition and Food Science, 53$^{rd}$ Conference, English Translation, 1999, p. 1.*
STN.pdf, 2008, pp. 1-8.*
Moran et al, Biochemistry, 2nd Edn., Prentice Hall, 1994, p. 10-8.*
Morimoto et al., "Role of nucleic acid as a nutritional factor—mainly concerning insulin-like actions -," Presentation summaries of the 53$^{rd}$ conference an scientific meetings of the Japanese Society of Nutrition and Food Science, p. 47 2E-06p, Apr. 20, 1999.

* cited by examiner

*Primary Examiner*—Shaojia Anna Jiang
*Assistant Examiner*—Ganapathy Krishnan
(74) *Attorney, Agent, or Firm*—Finnegan, Henderson, Farabow, Garrett & Dunner, L.L.P.

(57) ABSTRACT

An object of the invention is to provide a substance that activates saccharide uptake in epidermal cells and is thus expected to be effective in promoting skin cell neogenesis and metabolism. The invention provides a promoter for saccharide uptake in epidermal keratinocytes which comprises a purine base or a salt thereof as an active ingredient. The present invention further provides a method of promoting saccharide uptake in epidermal keratinocytes, comprising applying a purine base or a salt thereof to the skin.

8 Claims, 1 Drawing Sheet

SUGAR INTAKE PROMOTERS

TECHNICAL FIELD

The present invention relates to a promoter for saccharide uptake which has the action of promoting saccharide uptake in epidermal keratinocytes. The present invention further relates to a method of promoting saccharide uptake in epidermal keratinocytes.

BACKGROUND ART

The epidermis is composed of various types of cells such as epidermal keratinocytes, Langerhans cells and melanocytes layered from the horney layer to the stratum basale. Saccharide uptake in the epidermis, especially by epidermal keratinocytes, plays an important role in epidermal cell neogenesis, division and differentiation (cornification). Therefore, the activation of saccharide uptake in epidermal keratinocytes can promote skin turnover and metabolism and is thus expected to be effective for the prevention or elimination of melamine or like pigment deposits, cell activation, skin aging prevention, or the prevention or elimination of epidermal keratinocytic damage caused by UV radiation.

DISCLOSURE OF THE INVENTION

An object of the invention is to provide a substance that can promote saccharide uptake in epidermal cells. More specifically, an object of the invention is to provide a substance that can promote the uptake of saccharide, especially glucose, in epidermal cells, especially by epidermal keratinocytes. Another object of the invention is to provide a method of promoting saccharide uptake in epidermal keratinocytes.

The present inventors carried out research on the promotion of glucose uptake in epidermal cells and found that purine bases, especially adenosine monophosphate, i.e., the monophosphoric acid ester of adenosine, are excellent at promoting glucose uptake in epidermal keratinocytes. The present invention has been accomplished on the basis of this finding.

The present invention has the following embodiments:

(1) A promoter for saccharide uptake in epidermal keratinocytes, comprising a purine base or a salt thereof as an active ingredient.

(2) A promoter for saccharide uptake as defined in (1) wherein the purine base is at least one member selected from the group consisting of adenine, guanine, adenosine monophosphate, adenosine 5'-diphosphate, adenosine 5'-triphosphate, flavine adenine dinucleotide and nicotinamide adenine dinucleotide.

(3) A promoter for saccharide uptake as defined in (1) which contains the purine base is adenosine monophosphate.

(4) A promoter for saccharide uptake as defined in (1), which contains the purine base or salt thereof in a proportion of at least 0.1 wt. % per 100 wt. % of the promoter.

(5) A promoter for saccharide uptake as defined in (1), which contains the purine base or salt thereof in a proportion of 0.1 to 10 wt. % per 100 wt. % of the promoter.

(6) A promoter for saccharide uptake as defined in (1), which contains the purine base or salt thereof in a proportion of 0.1 to 7 wt. % per 100 wt. % of the promoter.

(7) A promoter for saccharide uptake as defined in (1), wherein the saccharide is at least one member selected from the group consisting of glucose, arabinose, xylose, mannose, galactose and fructose.

(8) A promoter for saccharide uptake as defined in (1), which has a pH in the range of 2 to 8.

(9) A promoter for saccharide uptake as defined in (1), which is in a form for external application.

(10) A method of promoting saccharide uptake in epidermal keratinocytes, comprising applying a purine base or a salt thereof to the skin.

(11) A method as defined in (10), wherein the purine base is at least one member selected from the group consisting of adenine, guanine, adenosine monophosphate, adenosine 5'-diphosphate, adenosine 5'-triphosphate, flavine adenine dinucleotide and nicotinamide adenine dinucleotide.

(12) A method as defined in (10), wherein the purine base is adenosine monophosphate.

(13) A method as defined in (10), wherein the saccharide is at least one member selected from the group consisting of glucose, arabinose, xylose, mannose, galactose and fructose.

(14) A method as defined in (10), which comprises applying to the skin a composition containing the purine base or salt thereof in a proportion of at least 0.1 wt. %.

(15) A method as defined in (10), which comprises applying to the skin a composition containing the purine base or salt thereof in a proportion of 0.1 to 10 wt. %.

(16) A method as defined in (10), which comprises applying to the skin a composition containing the purine base or salt thereof in a proportion of 0.1 to 7 wt. %.

(17) A method as defined in (14) wherein the composition has a pH in the range of 2 to 8.

(18) Use of a purine base or a salt thereof for preparing a promoter for saccharide uptake in epidermal keratinocytes.

(19) Use of a purine base or a salt thereof for promoting saccharide uptake in epidermal keratinocytes.

BEST MODE FOR CARRYING OUT THE INVENTION

Figure 1:
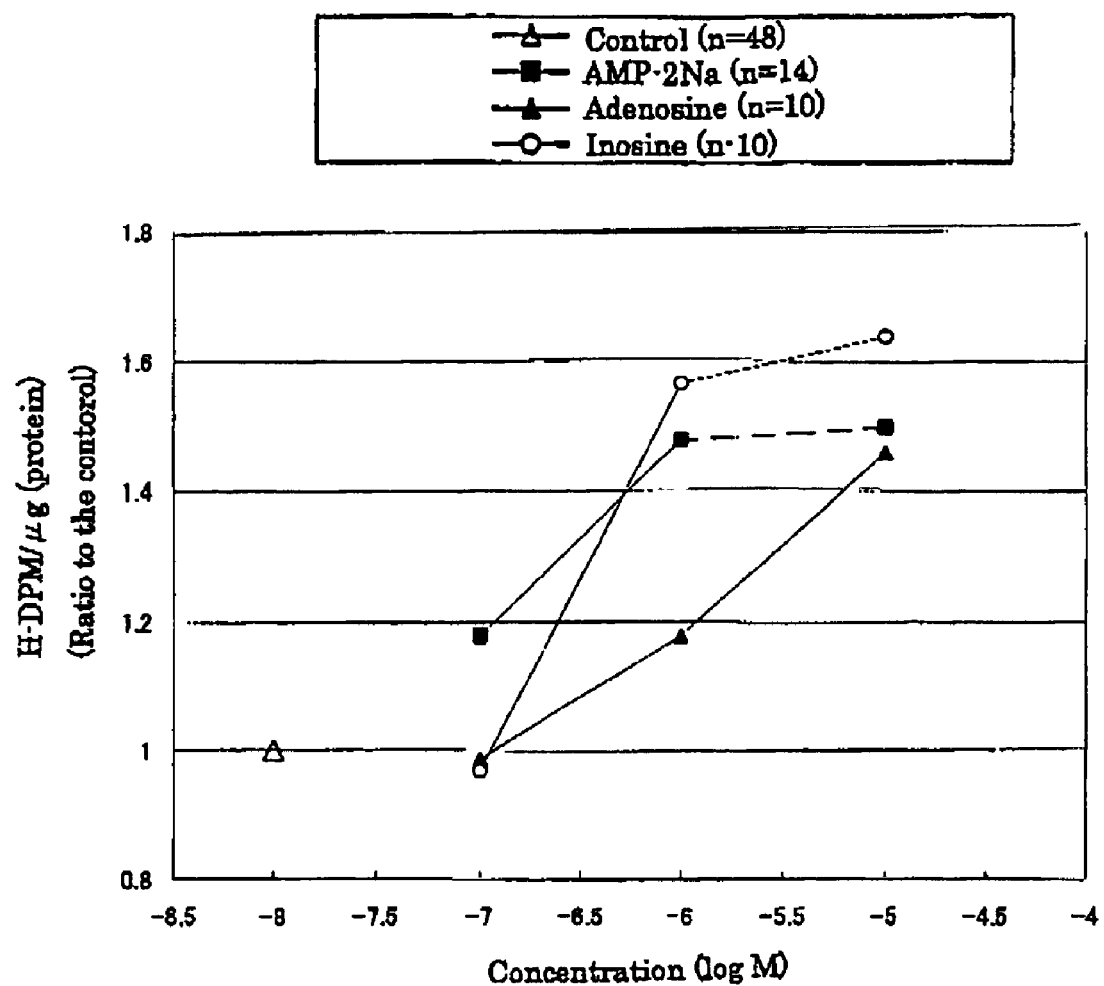
FIG. 1 shows the results of Experiment Example 1 examining AMP-2Na (-■-), adenosine (-▲-) and inosine (-○-) for their promotion effect on $^3$H-2-deoxyglucose (2-DG) uptake in epidermal keratinocytes. In the FIGURE, the abscissa designates the concentration (log M) of each purine base, and the ordinate designates the amount of uptaken 3H-2-deoxyglucose per μg of cellular protein (ratio of 2-deoxyglucose uptake amount relative to the amount of the control set as 1).

1. Promoter for Saccharide Uptake in Epidermal Keratinocytes

The promoter for saccharide uptake in epidermal keratinocytes of the invention comprises a purine base or a salt thereof as an active ingredient.

Purine base is a general term for purine and various purine derivatives having a purine nucleus. Examples include adenine, guanine, and their deaminated compounds (hypoxanthine, xanthine), adenosine, guanosine, inosine, adenosine phosphates (adenosine 2'-phosphate, adenosine 3'-phosphate, adenosine 5'-phosphate, adenosine 5'-diphosphate, adenosine 5'-triphosphate), guanosine phosphates (guanosine 3'-phosphate, guanosine 5'-phosphate, guanosine 5'-diphosphate, guanosine 5'-triphosphate), adenylosuccinic acid, xanthic acid, inosinic acid, flavine adenine dinucleotide (FAD), nicotinamide adenine dinucleotide (NAD) and the like. Examples of purine bases preferably used in the invention include adenine, guanine, adenosine monophosphates [adenosine 2'-phosphate, adenosine 3'-phosphate, adenosine 5'-phosphate (AMP)], adenosine 5'-diphosphate (ADP), adenosine 5'-triphosphate (ATP), flavine adenine dinucleotide (FAD) and nicotinamide adenine dinucleotide (NAD). Adenosine monophosphates are more preferable and adenosine 5'-phosphate (AMP) is particularly preferable.

In the invention, purine base salts can be used in place of or in combination with the purine bases. Examples of such purine base salts include alkali metal salts such as sodium salts and potassium salts; alkaline earth metal salts such as magnesium salts, calcium salts and barium salts; salts of basic amino acids such as arginine and lysine; ammonium and ammonium salts such as tricyclohexylammonium salts; and salts of alkanolamines such as monoethanolamine, diethanolamine, triethanolamine, monoisopropanolamine, diisopropanolamine and triisopropanolamine. Alkali metal salts such as sodium salts are preferable. Adenosine monophosphate monosodium and adenosine monophosphate disodium are particularly preferable.

The purine bases or salts thereof can be used singly or in combination of two or more. The manner of combination is not particularly restricted so long as it does not impair the effects of the invention.

The purine bases or salts thereof act on skin epidermal cells and, in particular, promote the saccharide uptake capability of epidermal keratinocytes. Accordingly, the purine bases or salts thereof can produce their effects by application to the skin, whereby the effects can be effectively utilized. The purine bases or salts thereof can be used alone as a promoter for saccharide uptake in epidermal keratinocytes. Alternatively, they can be used as active ingredients and formed into saccharide uptake-promoting cosmetics or external preparations for the skin (promoter for saccharide uptake) such as pharmaceutical or quasi-pharmaceutical products for external application by combination with cosmetically or pharmaceutically acceptable bases, carriers or additives. In the latter case, the proportion of purine base or salt thereof in the skin preparation is not particularly limited so long as the effects of the invention can be achieved. The purine base or salt thereof can usually be incorporated in a proportion of about 0.1 wt. % or more, and preferably about 0.5 wt. % or more, per 100 wt. % of the final product skin preparation (promoter for saccharide uptake). There is no upper limit on the proportion of the purine base or salt thereof so long as the preparation achieves the saccharide uptake promotion effects of the invention. The upper limit may be, for example, about 10 wt. %, preferably about 7 wt. %, and more preferably about 6 wt. %. The proportion of the purine base or salt thereof can suitably be selected using the above upper and lower limits as a guide. The proportion may be, for example, in the range of 0.1 to 10 wt. %, 0.1 to 7 wt. %, or 0.5 to 10 wt. %, per 100 wt. % of the final product skin preparation (promoter for saccharide uptake). The proportion is preferably in the range of 0.5 to 7 wt. %, and more preferably 1 to 6 wt. %, in view of product stability and balance with other components.

The promoter of the invention is particularly excellent in promoting the glucose uptake capability of epidermal cells. The targeted saccharide is not limited to glucose but also includes arabinose, xylose, mannose, galactose, fructose or like monosaccharides. The promoter for saccharide uptake of the invention has the action of promoting the uptake of at least one saccharide, particularly at least one monosaccharide, in epidermal keratinocytes but does not need to promote the uptake of all saccharides. Glucose is a particularly suitable saccharide.

The promoter for saccharide uptake of the invention may optionally contain various components usually added to external preparations, such as surfactants, solubilizing components, fats or oils, polyhydric alcohols, thickeners, antiseptics, colorants, dispersants, pH adjusters and aromatic substances. These components can be used singly or in combination of two or more.

Examples of usable surfactants include cationic surfactants, anionic surfactants, nonionic surfactants, and amphoteric surfactants.

Examples of solubilizing components include lower alcohols such as ethanol; polyhydric alcohols such as glycerol, ethylene glycol and propylene glycol; hydrogenated soybean phospholipid, polyoxyethylene sorbitan fatty acid ester, polyoxyethylene lanolin alcohol, polyoxyethylene castor oil, polyoxyethylene hydrogenated castor oil, polyoxyethylene sterol, polyoxyethylene alkyl ether, polyoxyethylene polyoxypropylene alkyl ether, polyoxyethylene alkyl phenyl ether and the like.

Examples of fats or oils include peanut oil, sesame oil, soybean oil, safflower oil, avocado oil, sunflower oil, corn oil, rapeseed oil, cottonseed oil, castor oil, camellia oil, coconut oil, olive oil, poppy oil, cacao oil, jojoba oil, beef tallow, lard, wool oil and like fats and oils; vaseline, liquid paraffin, squalane, α-olefin oligomer and like hydrocarbon liquid oils; isopropyl myristate, isopropyl isostearate, myristyl myristate, cetyl palmitate, cetyl isooctate, isocetyl myristate, n-butyl myristate, octyldodecyl myristate, isopropyl linolenate, propyl ricinoleate, isopropyl ricinoleate, isobutyl ricinoleate, heptyl ricinoleate, diethyl sebacate, diisopropyl adipate and like higher fatty acid esters; white beeswax, whale tallow, Japan tallow and like waxes; cetyl alcohol, stearyl alcohol, behenyl alcohol, batyl alcohol, chimyl alcohol and like higher aliphatic alcohols; waxes; stearic acid, oleic acid, palmitic acid and like higher fatty acids; methyl polysiloxane, dimethyl polysiloxane, methylphenyl polysiloxane, methyl hydrogen polysiloxane and like mono-, di-, or triglyceride mixtures of $C_{12-18}$ saturated or unsaturated fatty acids; linear silicones; decamethylcyclopentasiloxane, octamethylcyclotetrasiloxane, methylcyclosiloxane and like cyclic silicones; crosslinked methyl polysiloxane, crosslinked methylphenyl polysiloxane and like crosslinked silicones; and silicone oils such as silicones modified by polyoxyethylene, polyoxypropylene or the like. Hydrocarbon liquid oils such as vaseline, liquid paraffin, squalane, and α-olefin oligomer are preferable. When the oils are solid, it is preferable to use auxiliary resolvents.

Specific examples of polyhydric alcohols include glycerin, polyglycerins having a polymerization degree of 2 to 10 (e.g., diglycerin, triglycerin, tetraglycerin), ethylene glycol, diethylene glycol, polyethylene glycol, 1,3-butylene glycol, propylene glycol, dipropylene glycol, isoprene glycol, pentadiol, sorbitol, maltitol, fructose, and the like.

By adding optional components as described above to the purine base or salt thereof and optionally further adding other solvents, pharmaceutical bases or carriers usually used for external preparations, etc., the promoter for saccharide uptake of the invention can be made into various desired forms for external preparations such as pastes, mousses, gels, liquids, emulsions, suspensions, creams, ointments, sheets, aerosols and sprays. These products can be produced by conventional methods.

The promoter for saccharide uptake of the invention usually has a pH in the range of 2 to 8. In view of low irritation to the skin and mucosa and pleasant skin feeling upon use, it is preferable to have a pH in the range of 2 to 7, more preferably 3 to 7, and further more preferably a slightly acidic to neutral pH of 5 to 7.

The promoter for saccharide uptake of the invention is not specifically limited in form and purpose so long as it is in the form applicable to the skin, such as a cosmetic, pharmaceutical or quasi-pharmaceutical preparation for skin application. Examples include makeup cosmetics such as foundations, rouges, lip sticks, mascaras, eye shadows, eyeliners, face powders, eyebrow pencils and nail care products; basic skin care products such as emulsions, creams, lotions, oils and packs; washes such as facial washes, cleansing creams and body washes; hair cosmetics such as hairdressings and hair restorers; various external compositions such as wound healing agents, cleaning agents, cleaners, whitening agents, UV protectors and bath agents. Suitable amounts of these products can be applied to the skin one or more times in accordance with the user's age and sex, use, skin condition of the affected part, etc.

The promoter for saccharide uptake of the invention can promote saccharide uptake in epidermal keratinocytes by being applied, attached or sprayed onto the skin and is thus expected to be effective in promoting skin turnover and preventing or improving skin diseases or disorders, skin aging, etc. Skin diseases and disorders include spots, freckles, erythema, sunburn, dullness and like pigment (melanine) deposits, wrinkles, etc.

II. Method of Promoting Saccharide Uptake in Epidermal Keratinocytes

As described above, the purine base or salt thereof can promote saccharide uptake in epidermal keratinocytes. Thus the present invention provides a method of promoting saccharide uptake in epidermal keratinocytes using the purine base or salt thereof.

The method of promoting saccharide uptake in epidermal keratinocytes according to the invention can be carried out by applying to the skin a purine base or a salt thereof by itself, or as a composition containing the purine base or salt thereof.

Purine bases or salts thereof usable in the method of the invention are the same as used in the above promoter for saccharide uptake, and the targeted saccharides are also the same as those of the promoter for saccharide uptake described above.

In the method of the invention, the method of applying the purine base or salt thereof to the skin is not specifically restricted so long as the purine base or salt thereof is brought into contact with the targeted skin portion. For example, the purine base or salt thereof, alone, or a composition containing the substance as an active ingredient and further containing pharmaceutically or cosmetically acceptable bases, carriers or additives, can be applied or sprayed onto the skin or attached to the skin in the form of a patch. When used in the form of a composition, the proportion of the purine base or salt thereof is not specifically limited so long as the effects of the invention can be achieved. The purine base or salt thereof can usually be incorporated in a proportion of about 0.1 wt. % or more, and preferably about 0.5 wt. % or more, per 100 wt. % of the composition. There is no upper limit on the proportion of the purine base or salt thereof so long as the saccharide uptake promotion effect of the invention can be achieved. The upper limit may be, for example, about 10 wt. %, preferably about 7 wt. %, and more preferably about 6 wt. %. The proportion of the purine base or salt thereof can suitably be selected using the above-mentioned upper and lower limits as a guide, and may be, for example, in the range of 0.1 to 10 wt. %, 0.1 to 7 wt. %, 0.5 to 10 wt. %, per 100 wt. % of the composition. The proportion is preferably in the range of 0.5 to 7 wt. %, and more preferably 1 to 6 wt. %. The composition usually has a pH in the range of 2 to 8. In view of low irritation to the skin and mucosa and pleasant skin feeling upon use, it is preferable to have a pH in the range of 2 to 7, more preferably 3 to 7, and further more preferably a weakly acidic pH of 5 to 7.

Modes of carrying out the method of the invention include, for example, applying a purine base or salt thereof to the skin by using various external compositions containing the purine base or salt thereof (e.g., makeup cosmetics such as foundations, rouges, lip sticks, mascaras, eye shadows, eyeliners, face powders, eyebrow pencils and nail care products; basic skin care products such as emulsions, creams, lotions, oils and packs; washes such as facial washes, cleansing creams and body washes; hair cosmetics such as hairdressings and hair restorers; wound healing agents, cleaning agents, cleaners, whitening agents, UV protectors and bath agents).

The amount of purine base or salt thereof and the number of times it is applied are not specifically limited. For example, a suitable amount of purine base or salt thereof can be applied to the skin once, or several times a day, in accordance with the kind of purine base or salt thereof, the user's age and sex, use, skin condition of the affected part, application form, etc.

EXAMPLES

The following experiment example and examples are illustrative of the invention and are not intended to be construed as limitations on the scope of the invention. In these examples, percentages are all by weight unless otherwise specified.

Experiment Example 1

The influence of purine base on glucose uptake in epidermal keratinocytes was examined using adenosine 5'-phosphate-2Na (AMP-2Na), adenosine and inosine as test compounds. As a control, the experiment was carried out in a similar manner without using the test compound.

<Method for Preparing Reagents, etc.>

1. Preparation of Human Epidermal Keratinocytes

Human epidermal keratinocyates (normal human neonatal foreskin epidermal keratinocytes, "Epidercell NHEK(F)", product of Kurabo industries, Ltd.) were initially cultured in a 10-cm petri dish and stored in a frozen state until use. At the time of use, the cryopreserved cells were cultured on a 24-well plate for about 6 to 7 days and subjected to this experiment when the cells were 70-80% confluent.

2. Preparation of 1% BSA/Glucose-Free Medium (pH 7.4)

A glucose-free medium was prepared by adding to a serum-free medium for the growth of epidermal keratinocytes ("HuMedia-KG2", special ordered medium, product of Kurabo Industries, Ltd.) 1 ml of calcium solution and 0.1 ml of phenol red packaged with the medium product. Bovine serum albumin (BSA) treated with activated carbon to remove impurities was added to the medium to become a concentration of 1% and the medium was adjusted to pH 7.4 with NaOH.

3. Preparation of 3H-2-deoxyglucose Solution 1 ml of 10 mM 2-deoxyglucose, 60 µl of 250 µCi/250 µl $^3$H-2-deoxyglucose and 940 µl of 1% BSA/glucose-free medium (pH 7.4) were mixed.

<Experimental Method>

Epidermal keratinocytes cultured in a 24-well plate were washed with PBS(−) ($Ca^{2+}$ and $Mg^{2+}$ free phosphate buffered saline) three times. After addition of serum-free medium for the growth of epidermal keratinocytes ("HuMedia-KG2", special ordered medium, product of Kurabo Industries, Ltd.), the cells were cultured for 2 hours and then washed with PBS(−) three times. After addition of 1 ml of 1% BSA/glucose-free medium (pH 7.4) in which the test compound was dissolved, the cells were cultured for 30 minutes and then 20 µl of $^3$H-2-deoxyglucose solution was added per ml of the medium. The cells were allowed to stand for 10 minutes and then washed with ice-cooled glucose-containing PBS(−) three times. After addition of 0.5 ml of 0.1N NaOH containing 0.1% SDS, the cells ware allowed to stand in a static condition for at least 2 hours to produce a cell lysate solution. 0.5 ml of 0.11N HCl containing 0.1% SDS was added to acidify the cell lysis solution. 80 μl of the cell lysate solution was used for protein assay ("DC Protein Assay", product of Bio-Rad), and 750 μl of the same was placed into a glass bottle. 20 ml of a liquid scintillation cocktail (ACS-II, product of Amersham) was added. After gently stirring the mixture, radioactivity was assayed using the liquid scintillation counter. The radioactivity per unit amount of protein was determined from the measured radioactivity and the amount of $^3$H-2-deoxyglucose uptake (H-DPM (μg)/μg protein) was calculated by subtracting the radioactivity due to non-specific 3H-2-deoxyglucose uptake.

<Results>

The above experiment was carried out twice and the mean averages were calculated. For comparison with the control, each value was converted to a ratio to the control value set as 1. FIG. 1 shows the results. In FIG. 1, the abscissa designates the concentration (log M) of each purine base (AMP-2Na, adenosine, inosine), and the ordinate designates the ratio of cellular 2-deoxyglucose uptake amount (H-DPM (μg)/μg protein) relative to the control set as 1.

AMP-2Na at concentrations of $10^{-6}$M and $10^{-5}$M promoted glucose uptake about 1.48 times and about 1.61 times respectively relative to the (test compound-free) control in the first experiment. Also in the second experiment, AMP-2Na at concentrations of $10^{-6}$M and $10^{-5}$M promoted the uptake about 1.48 times and about 1.43 times over the control.

It was confirmed that, as with AMP-2Na, adenosine and inosine also have the action of promoting epidermal keratinocytic glucose uptake. However, as shown in FIG. 1, when compared at the same concentration, AMP-2Na promoted glucose uptake more effectively than adenosine at low concentration. The promotion effect of AMP-2Na at a concentration of $10^{-6}$M was about 1.16 times higher than that of adenosine at the same concentration in the first experiment, and about 1.32 times higher in the second experiment, which are statistically significant differences (first experiment: $p<0.05$, second experiment: $p<0.05$). It can also be said that AMP-2Na promotes glucose uptake more effectively than inosine at low concentration ($10^{-7}$M).

The above results show that purine bases such as AMP-2Na, adenosine and inosine have the action of promoting the glucose uptake capability of epidermal keratinocytes and in particular, AMP-2Na achieves this effect even at a low concentration. Thus purine bases are excellent at promoting glucose uptake capability.

Example 1

Emulsion

EXAMPLE 1

| Emulsion | |
|---|---|
| Carboxy vinyl polymer | 0.3 (%) |
| AMP-2Na | 1.5 |
| Decaglycerol monomyristate | 2.0 |
| Squalane | 5.0 |

EXAMPLE 1-continued

| Emulsion | |
|---|---|
| Refined glycerin | 6.0 |
| pH adjuster | the amount required to adjust the pH to 7 |
| Antiseptic | appropriate amount |
| Purified water | the balance |
| Total | 100.0% |

Example 2

Skin Lotion

EXAMPLE 2

| Skin lotion | |
|---|---|
| Polyoxyethylene (E.O. 60) hydrogenated castor oil | 0.7 (%) |
| AMP-2Na | 3.0 |
| Ethanol | 5.0 |
| Glycerin | 2.0 |
| pH adjuster | the amount required to adjust the pH to 7 |
| Antiseptic | appropriate amount |
| Aromatic substance | appropriate amount |
| Purified water | the balance |
| Total | 100.0% |

Example 3

Hair Restorer

EXAMPLE 3

| Hair restorer | |
|---|---|
| Salicylic acid | 0.1 (%) |
| AMP-2Na | 10.0 |
| Ethanol | 20.0 |
| Glycerin | 2.0 |
| pH adjuster | the amount required to adjust the pH to 7 |
| Antiseptic | appropriate amount |
| Aromatic substance | appropriate amount |
| Purified water | the balance |
| Total | 100.0% |

INDUSTRIAL APPLICABILITY

According to the present invention, the saccharide uptake capability of epidermal keratinocytes can be promoted and resultant skin turnover and metabolism promotion effects can be expected. The promoter for saccharide uptake of the invention is therefore useful as skin cosmetics, pharmaceutical or quasi-pharmaceutical preparations for external application expected to be effective in skin anti-aging and skin beautification, i.e., preventing fine wrinkles, giving elasticity to the skin, preventing pigmentation, maintaining and promoting the whitening of the skin, etc.

The invention claimed is:

1. A method of promoting glucose uptake in human skin epidermal keratinocytes, comprising applying a suitable amount of a composition comprising adenosine 5'-monophosphate or a salt thereof in a proportion of 1 to 6 wt. % to the skin.

2. A method according to claim 1, wherein the adenosine 5'-monophosphate or a salt thereof is the sodium salt of adenosine 5'-monophosphate.

3. A method according to claim 1, wherein the composition has a pH in the range of 2 to 8.

4. A method of treating a human patient in need of activation of glucose uptake in skin epidermal keratinocytes comprising applying a suitable amount of a composition comprising adenosine 5'-monophosphate or a salt thereof in a proportion of 1 to 6 wt. % to the skin of said patient.

5. A method according to claim 4, wherein the adenosine 5'-monophosphate or a salt thereof is the sodium salt of adenosine 5'-monophosphate.

6. A method according to claim 4, wherein the composition has a pH in the range of 2 to 8.

7. A method of promoting glucose uptake in human skin epidermal keratinocytes, comprising applying a suitable amount of a composition comprising adenosine 5'-monophosphate or a salt thereof in a proportion of 1 to 6 wt. % to the skin of the human in need of activation of glucose uptake in the skin epidermal keratinocytes.

8. A method of promoting skin turnover, comprising applying a suitable amount of a composition comprising adenosine 5'-monophosphate or a salt thereof in a proportion of 1 to 6 wt. % to the skin of the human in need of promotion of skin turnover by promoting glucose uptake in human skin epidermal keratinocytes.

* * * * *